US008510240B2

(12) United States Patent
Patrao et al.

(10) Patent No.: US 8,510,240 B2
(45) Date of Patent: Aug. 13, 2013

(54) SYSTEM AND METHOD FOR AUTOMATICALLY GENERATING A MEDICAL CODE

(75) Inventors: Rajesh Lawrence Patrao, Mangalore (IN); Gururaj Bhimsen Rao, Mumbai (IN); Guruprasad Holla, Bangalore (IN)

(73) Assignee: Infosys Limited (IN)

( * ) Notice: Subject to any disclaimer, the term of this patent is extended or adjusted under 35 U.S.C. 154(b) by 234 days.

(21) Appl. No.: 13/179,607

(22) Filed: Jul. 11, 2011

(65) Prior Publication Data

US 2012/0254083 A1 Oct. 4, 2012

(30) Foreign Application Priority Data

Mar. 31, 2011 (IN) .............................. 1069/CHE/2011

(51) Int. Cl.
*G06F 15/18* (2006.01)
(52) U.S. Cl.
USPC ............................................................ 706/14

(58) Field of Classification Search
None
See application file for complete search history.

(56) References Cited

U.S. PATENT DOCUMENTS

2008/0288292 A1* 11/2008 Bi et al. ............................ 705/3
2012/0110016 A1* 5/2012 Phillips ......................... 707/780

OTHER PUBLICATIONS

Henley et al. "Injury severity scaling", AIHW Injury Technical Paper Series No. 10, pp. 26.*

* cited by examiner

*Primary Examiner* — Li-Wu Chang
(74) *Attorney, Agent, or Firm* — Cantor Colburn LLP (57) ABSTRACT

Disclosed herein is a system which address the problem of multiple mappings of a source ICD code to a target ICD code by using an adaptive mechanism to automatically convert to a target ICD code with the help of accompanying data and associated rules. The mechanism is based on analysis of the ICD code description, and analysis of accompanying data to determine a set of parameters to assist in the conversion. The rules are assigned numerical values to indicate the confidence of conversion. An adaptive mechanism is also disclosed that automatically tracks user overrides to refine the rules and the indicator values over time.

35 Claims, 7 Drawing Sheets

FIG. 1 (Prior Art)

110: ICD-10-PCS Source: 0273ZZ Dilation of Coronary Artery, Four or More Sites, Percutaneous Approach = ICD-9-CM Target: 00.66 PTCA or coronary atherectomy AND 00.40 Procedure on single vessel OR 00.41 Procedure on two vessels OR 00.42 Procedure on three vessels OR 00.43 Procedure on four or more vessels OR 00.44 Procedure on vessel bifurcation 120: ICD-9-CM Source: 65.63 Laparoscopic removal of both ovaries and tubes at same operative episode = ICD-10-PCS Target: 0UT24ZZ Resection of bilateral ovaries, percutaneous endoscopic approach AND 0UT74ZZ Resection of bilateral fallopian tubes, percutaneous endoscopic approach Source: General Equivalence Mapping (GEM Mapping)

SYSTEM AND METHOD FOR AUTOMATICALLY GENERATING A MEDICAL CODE

FIELD OF THE INVENTION

This present disclosure relates in general to the field of medical information management, and more particularly, to a system and method for processing an incoming ICD code by applying associated rules and mapping information for use in supporting healthcare or other organization, for example.

BACKGROUND OF THE INVENTION

Classification involves the categorization of relevant concepts for the purposes of systematic recording or analysis. The categorization is based on one or more logical rules. To this end WHO has developed reference classifications that can be used to describe the health state of a person at a particular point in time. Diseases and other related health problems, such as symptoms and injury, are classified in the International Classification of Diseases (ICD). A classification of diseases may be defined as a system of categories to which morbid entities are assigned according to established criteria. The ICD is used to translate diagnosis of diseases and other health problems from words into an alphanumeric code, which permits easy storage, retrieval and analysis of data.

The International Classification of Diseases 10th Revision Procedure Classification System (ICD-10-PCS) and ICD-10-CM have been developed as a replacement of the International Classification of Diseases 9th Revision (ICD-9-CM). In ICD-9-CM, the methodology for assigning a code is the same for diagnosis code and procedure code. ICD-10-CM and ICD-10-PCS use different methodologies for assigning codes. ICD-10-CM defines the code set used to report inpatient and outpatient diagnoses. ICD-10-PCS defines the code set used to report inpatient procedures. The traditional ICD structure has been retained but an alphanumeric coding scheme replaces the previous numeric one. This provides a larger coding frame and leaves room for future revision without disruption of the numbering system.

Mapping from a source or a reference terminology to another version of the classification is not straightforward i.e. one source ICD code is linked to one or more target ICD codes. ICD-10 is much more specific, for diagnoses, there are 14,025 ICD-9-CM codes and 68,069 ICD-10-CM codes; and for procedures, there are 3,824 ICD-9-CM codes and 72,589 ICD-10-PCS. Therefore, one ICD-9-CM diagnosis code is represented by multiple ICD-10 diagnosis code or procedure codes and one ICD-10 Diagnosis Code or Procedure Code is represented by multiple ICD-9-CM codes.

In US, the Centers for Medicare & Medicaid Services (CMS) and the Centers for Disease Control and Prevention has created the national version of the General Equivalence Mappings (GEM) to ensure that consistency in national data is maintained. Oct. 1, 2013 is the compliance date for implementation of ICD-10 for all covered entities. Mapping from one ICD version to another may give multiple codes rather than a mirror image or a single code. The GEMs can be used by anyone who wants to convert coded data, including, but not limited to, payers, providers, medical researchers, informatics professionals, coding professionals, organizations. For example, in coding individual claims, it will be more efficient and accurate to select the appropriate code(s) from the reference mapping by using associated medical record documentation.

Disclosed herein is a system which address the problem of multiple mappings of a source ICD code to a target ICD code by using an adaptive mechanism to automatically convert to a target ICD code with the help of accompanying data and associated rules.

SUMMARY OF THE INVENTION

Aspects of the disclosure relate to a system and method for automatic conversion of a source ICD code to one or more target ICD codes. An implementation of the disclosure addresses the problem of the 1:n mapping between different versions of ICD by using the accompanying data and associated rules to generate one or more target ICD code.

According to the disclosed system, the system comprises a token module to generate a set of tokens from the target ICD code descriptions. A rule engine compares these tokens to medical notes to select the applicable scenario and choice list for that particular source ICD code.

Accordingly, another aspect of the disclosure is to generate a single ICD code as an output by comparing the one or more potential target ICD codes with an upper and lower threshold value.

In another aspect of the disclosure, the ICD code descriptions are analyzed to a token repository.

In yet another aspect of the disclosure, an adaptive engine is provided to monitor user overrides, analyze information from an input file to obtain correlation factors and accordingly suggest changes to the rules and the workflow.

The above as well as additional aspects and advantages of the disclosure will become apparent in the following detailed written description.

BRIEF DESCRIPTION OF THE DRAWINGS

Aspects of the disclosure will be better understood with the accompanying drawings.

FIG. 6 is an illustrative example of the GEM Mapping of ICD-9-CM code 304 for Radial Laryngectomy.

DETAILED DESCRIPTION OF THE INVENTION

As used herein, the term 'Backward Mapping' means mapping from a later version of an ICD code set to an earlier version of an ICD code set.

As used herein, the term 'Choice list' means the conventional entry in the GEM denoting, in a combination entry, a list of one or more codes in the target code set from which one code must be chosen to satisfy the equivalent meaning of a code in the source code set. A choice list contains one or more codes in the target code set that express a portion of the meaning of the code in the source code set. A code must be included from a choice list in a scenario to satisfy the equivalent meaning of a code in the source code set.

As used herein, the term 'Combination Entry' means an entry in the GEM for which a code in the source code set must be linked to more than one code option in the target code set.

As used herein, the term 'Forward Mapping' means mapping from an earlier version of an ICD code set to a later version of an ICD code set.

As used herein, the term 'Identifier Tokens' are singular words uniquely identified within a choice list or within a particular virtual scenario.

As used herein, the term 'Identifier Slop' means the maximum distance between identifier tokens while searching. It is calculated as 1.5*number of words in the description of the choice in the choice list which has the description having the highest number of words.

As used herein, the term 'Identifier Weightage' means the attribute weightage to be assigned when the identifier level search is successful.

As used herein, the term 'Scenario' means the conventional entry in the GEM denoting, in a combination entry, a collection of codes from the target code set containing the necessary codes that combined as directed will satisfy the equivalent meaning of a code in the source code set. A scenario identifies one variation of the procedure or diagnosis.

As used herein, the term 'Scenario Slop' means the maximum distance between scenario tokens while searching. It is calculated as 1.5*number of words in the description of the choice among all the choice lists in the scenario, which has the description having the highest number of words.

As used herein, the term 'Scenario Token' means data specific and unique to a scenario which will help in narrowing down to the specific scenario.

As used herein, the term 'Scenario Weightage' means the attribute weightage to be assigned when the scenario level search is successful i.e. when a scenario (or scenario data) is found As used herein, the term 'Source Code Set' means the code set of origin in the mapping i.e. the set being mapped from.

As used herein, the term 'Supplementary Tokens' means a common sub-sequence within a choice list.

As used herein, the term 'Supplementary Slop' means the maximum distance between supplementary tokens while searching. It is calculated as 1.5*number of words in the description of the choice among all the choice lists in the scenario, which has the description having the highest number of words.

As used herein, the term 'Target Code Description' means the descriptions of the scenarios and choice lists as per the GEM mapping, at the code level.

As used herein, the term 'Target Code Set' means the destination code set in the mapping i.e. the set being mapped to.

As used herein, the term 'Virtual Scenario' is applicable for each non-multiple scenario. In such cases, for ease of searching, a very large choice list is divided into a number of logically similar groups. Each such group is called a Virtual Scenario.

Figure 1:
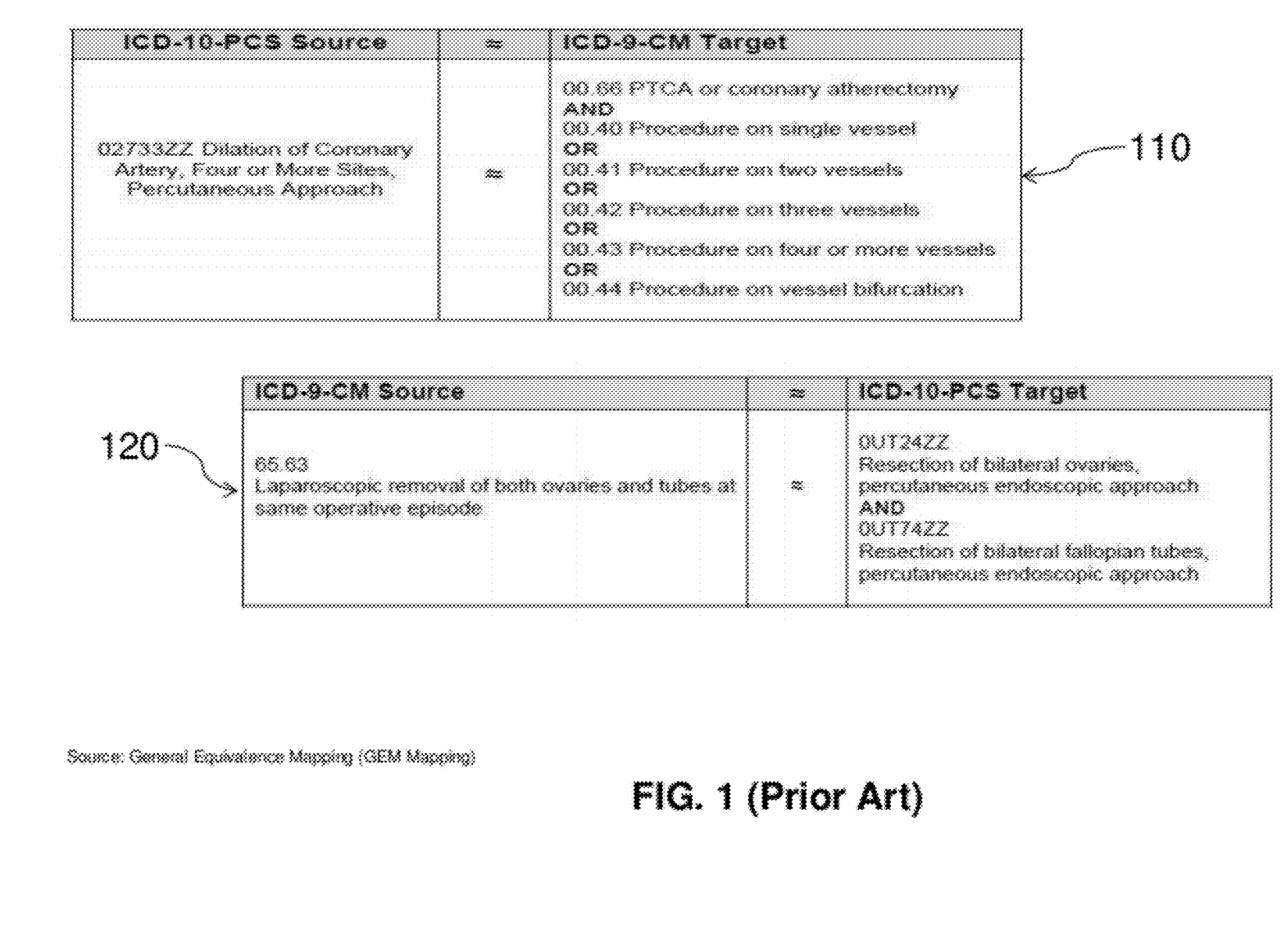
FIG. 1 is representative of the reference mapping from one ICD code set to another.

The disclosed system can be applied to both, forward mapping and backward mapping, with the objective of automatically finding the correct set of target ICD code(s) from the source ICD code. The basis of the system is the GEM provided by CMS. For the purpose of an illustration, FIG. 1 (Prior Art) is representative of the reference mapping from one ICD code set to another. 110 shows a single ICD-10-PCS source code set on the left side with multiple mappings of the same to the ICD-9-CM target code set on the right side. Similarly, 120 shows a single ICD-9-CM source code set on the left side with multiple mappings of the same to the ICD-10-PCS target code set on the right side. ICD-10 is much more specific, for diagnoses, there are 14,025 ICD-9-CM codes and 68,069 ICD-10-CM codes; and for procedures, there are 3,824 ICD-9-CM codes and 72,589 ICD-10-PCS. Therefore, one ICD-9-CM diagnosis or procedure code, may be represented by multiple ICD-10 diagnosis code or procedure codes and one ICD-10 Diagnosis Code or Procedure Code may be represented by multiple ICD-9-CM codes.

Figure 2:
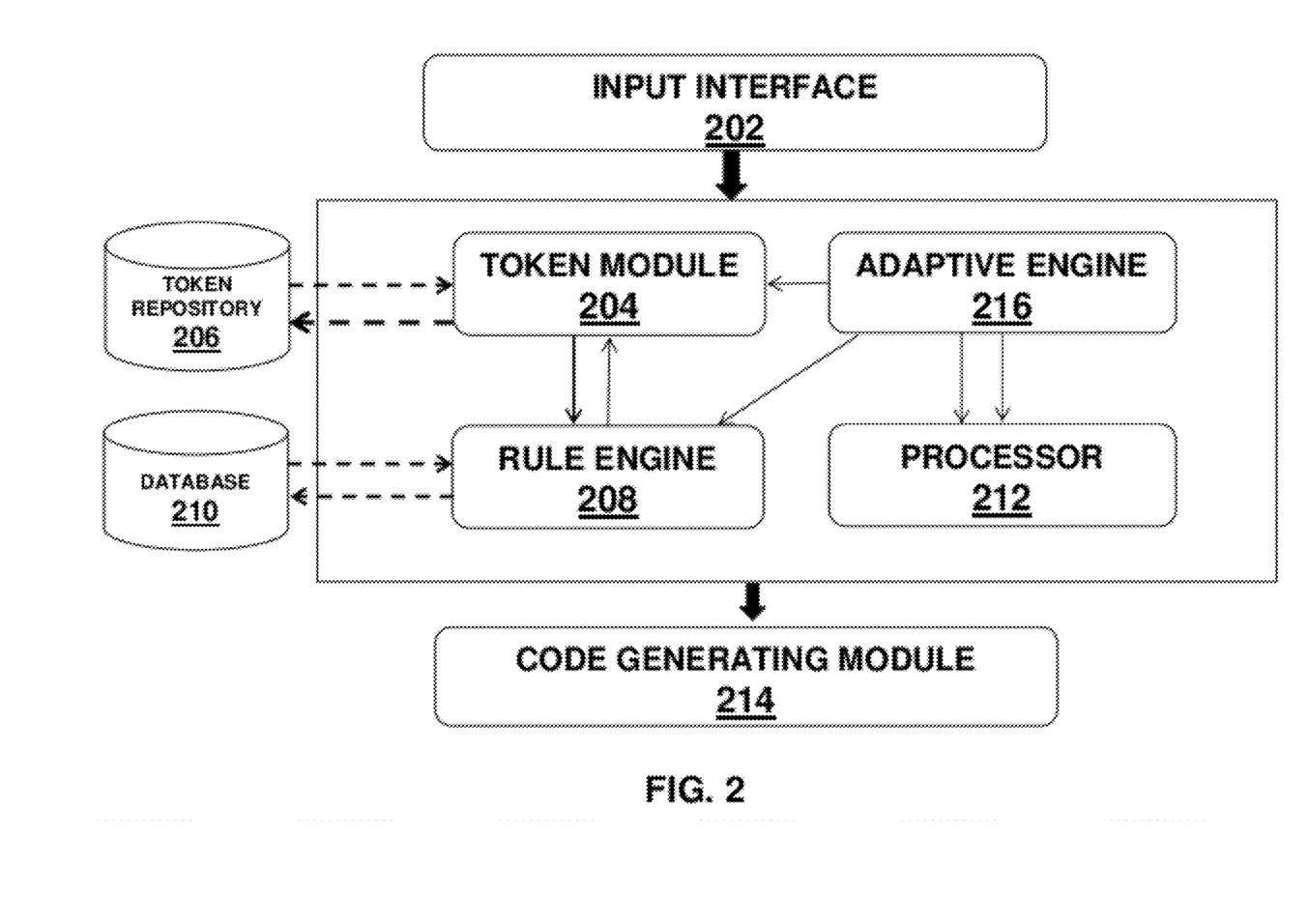
FIG. 2 is a block diagram depicting the automated conversion from a source ICD code to a target ICD code.

FIG. 2 is a block diagram of a system depicting the automated conversion from a source ICD code to a target ICD code. The input interface 202 accepts data in the form of a file or a code. Tokens are generated using the scenario and choice list of each of the target ICD codes using the token module 204. The system may be configured to store these tokens in a token repository 206. Since the generated tokens can be optionally stored in a repository 206, these pre-generated tokens can be used for subsequent conversions of a source ICD code to a target ICD code. The system then invokes the rules 208 to compare the set of tokens with a set of configured parameters. These parameters may include information from the claims or medical notes, for example. In one embodiment, the system invokes the rules 208 to compare the set of tokens with medical notes. A database 210 may be used provide to store information about the invoked rules. A processor 212 calculates a total code score for the selected scenarios and choice lists and sends the results to the code generating module 214. The system may also contain an Adaptive Engine 216. The Adaptive Engine monitors user overrides, analyses available information to obtain correlation factors and suggests changes to the rules repository and workflows.

Figure 3:
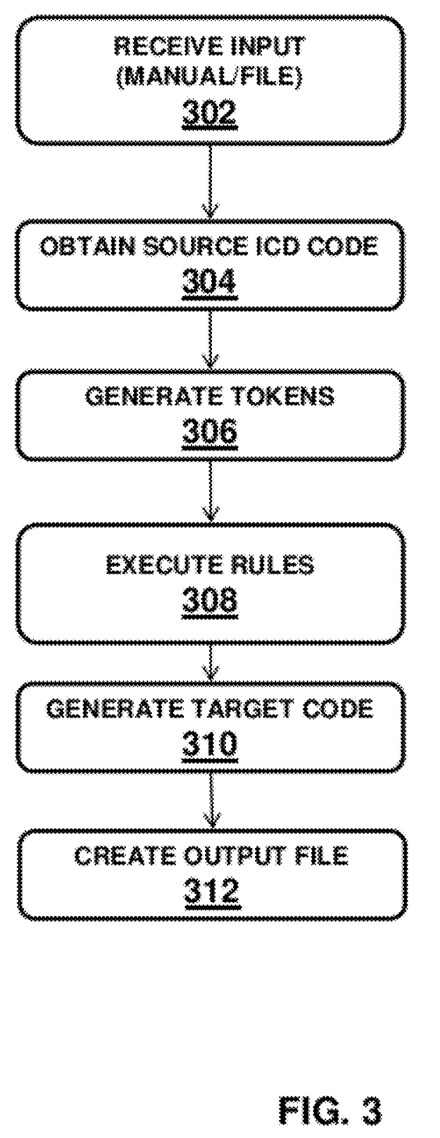
FIG. 3 gives an overview of the method used to automatically find and assign the target ICD code(s).

FIG. 3 is a schematic representation of the method used to automatically locate the target ICD codes. For every source ICD code (both, PCS and CM), the GEM mapping of the source ICD code is determined as per the GEM system. Input 302 can be accepted in the form of a file or a code. The file is then parsed to obtain the ICD codes 304 which will serve as an input for the automated process for finding the correct set of target codes. The file can be received in a variety of digital formats, including, but not limited to Electronic Data Interchange (EDI) format or Uniform Bill (UB). The file is analyzed to obtain the source ICD code which has to be mapped to a target ICD code. The file may also be analyzed to obtain a plurality of additional information parameters that will be passed to the rule engine to make a decision for the conversion. The additional parameters may include, but not limited to, hospital information, medical notes, patient demographics or historical data. Tokens 306 are obtained from the tokens module 204 using the scenario and choice list of each of the target ICD codes. Rules 308 to be implemented on the source ICD code are invoked by the rules engine 208. Target ICD codes are generated in the form of an output 310 or the input files 302 are updated with the converted code at the appropriate position in the file 312.

Figure 4:
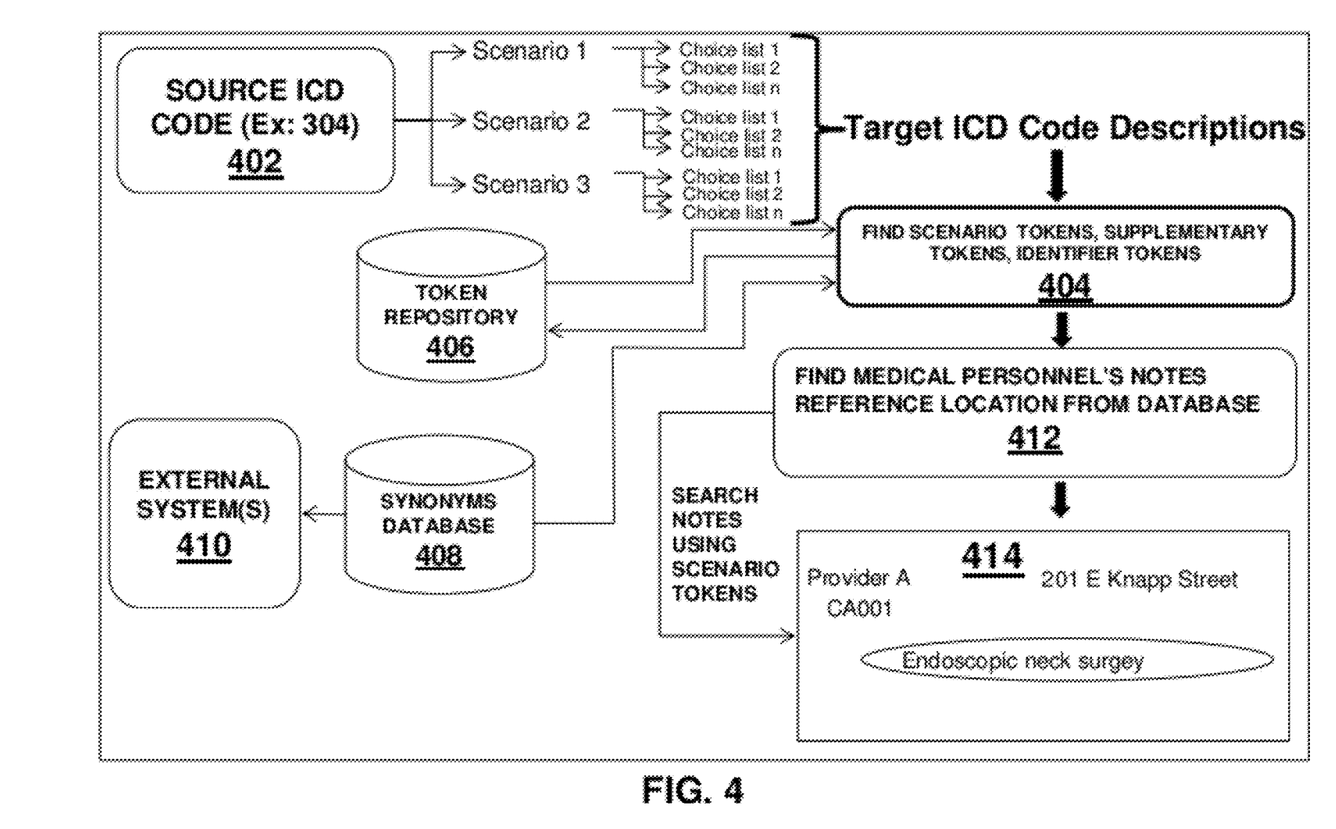
FIG. 4 is an exemplary representation of the token module.

FIG. 4 is an exemplary representation of the token module 204 which will generate tokens 306. A source ICD code 402 is represented by multiple equivalent target ICD codes. The target ICD code descriptions are used to generate three sets of tokens 404 namely, scenario tokens, supplementary tokens and identifier tokens. The scenario tokens, supplementary tokens and identifier tokens may also be generated using synonyms from external system(s) 410. These tokens may be optionally configured to be stored in a token repository 406 for usage of these in subsequent instances. Each set of tokens i.e. scenario tokens, supplementary tokens and identifier tokens are compared against the medical notes 414. System will search for the supplementary tokens and then search for the identifier in the proximity of supplementary tokens. The reference location of the medical notes may be configured in the database 412. These notes should preferably contain data with terminologies and words similar to the ICD code set.

There may be situations where the medical notes might contain short forms, for example, "Th" for thyroid. However since the ICD description contains the full forms, a data dictionary can be created to serve as an input for the repository of words and their full forms. The incoming medical notes may then be compared by looking up at the data dictionary. Rules to this effect can be configured in the database. Similarly, a list of stop words, which should be ignored while search, may also be created to enable an effective comparison of the scenario tokens, supplementary tokens and identifier tokens with the medical notes.

Figure 5:
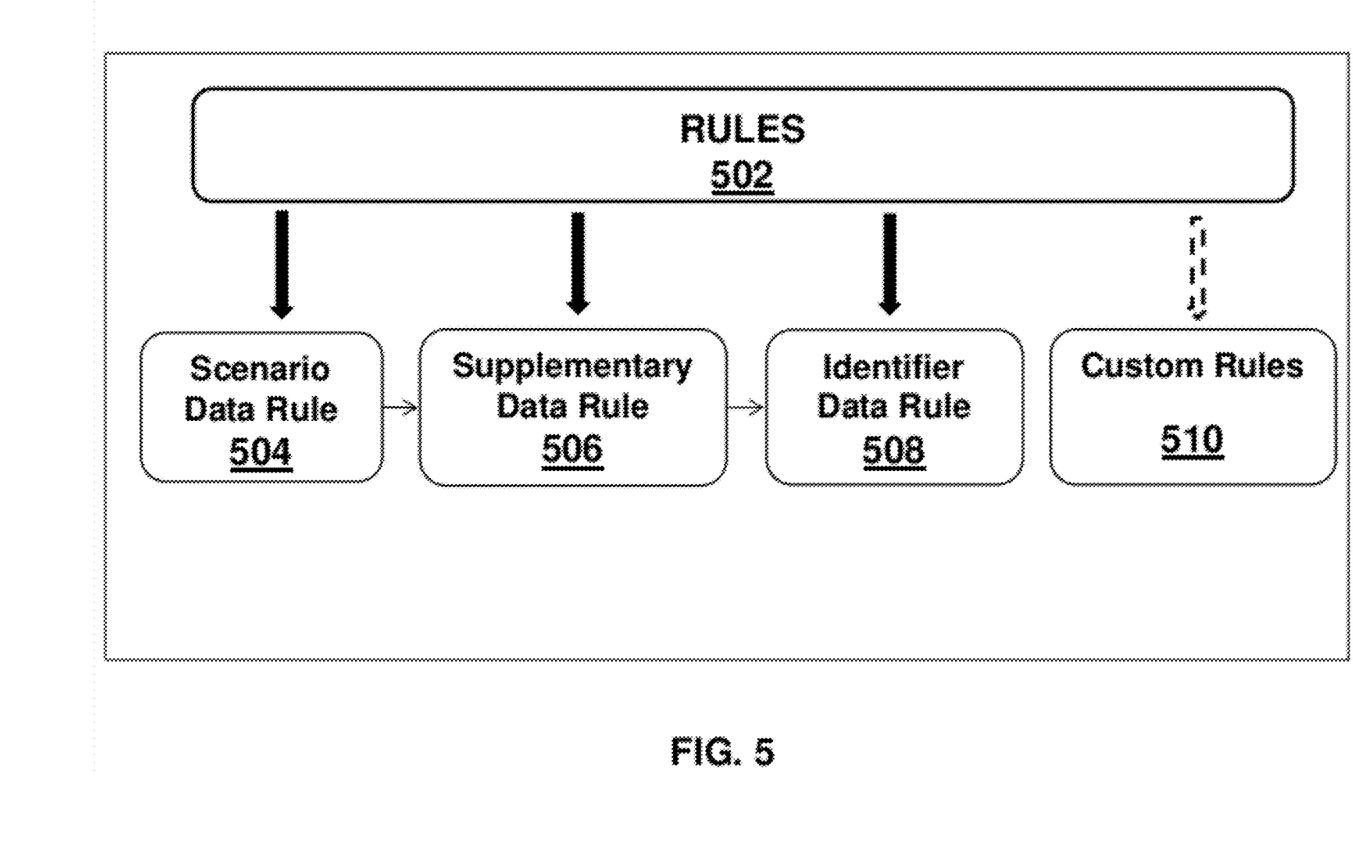
FIG. 5 is a block diagram representing the invoked rules.

FIG. 5 is a block diagram representing the rules invoked by the rules engine 208. These represent a hierarchy of rules which are numerical indicators of the certainty of conversion. These rules 502 can be customized and arranged in a workflow which will allow for hierarchical application of these rules. The order of execution of the associated rules i.e. default rules or customized rules 510 can be defined. There are three main rules; Scenario Data Rule 504. Supplementary Data Rule 506 and the Identifier Data Rule 508. It is to be noted that the number of rules or the order can be configured. The system can also be configured to not execute further rules if the certainty of conversion of a code obtained by the execution of one rule, for example, is sufficient. The scenario data rule 504 is executed to determine the one or more scenarios from multiple equivalent target ICD codes. Once the scenarios are selected, the supplementary data rule 506 and the identifier data rule 508 are executed to determine the applicable choice list.

FIG. 6 (Prior Art) is an illustrative example of the GEM Mapping of ICD-9-CM code 304 for Radial Laryngectomy. There are three scenarios of this code in the equivalent target mapping of the source ICD code. Each scenario contains multiple choice lists. A scenario is subdivided into two or more choice lists of codes in the target code set. These are the codes that must be linked together in an applied mapping to satisfy the equivalent meaning of the code in the source code set. The scenario data rule 504, will be used to apply the tokens 306 generated by the tokens module 204 on the notes. Based on the successful comparison of these tokens against the medical notes, one or more scenarios will be selected by the system. The selection of these one or more scenarios may also be dependent for example, on the degree of match configured in the system. The Supplementary Data Rule 506 and the Identifier Data Rule 508 are then executed within the choice lists of these one or more selected scenarios to determine the applicable choice lists.

Figure 7:
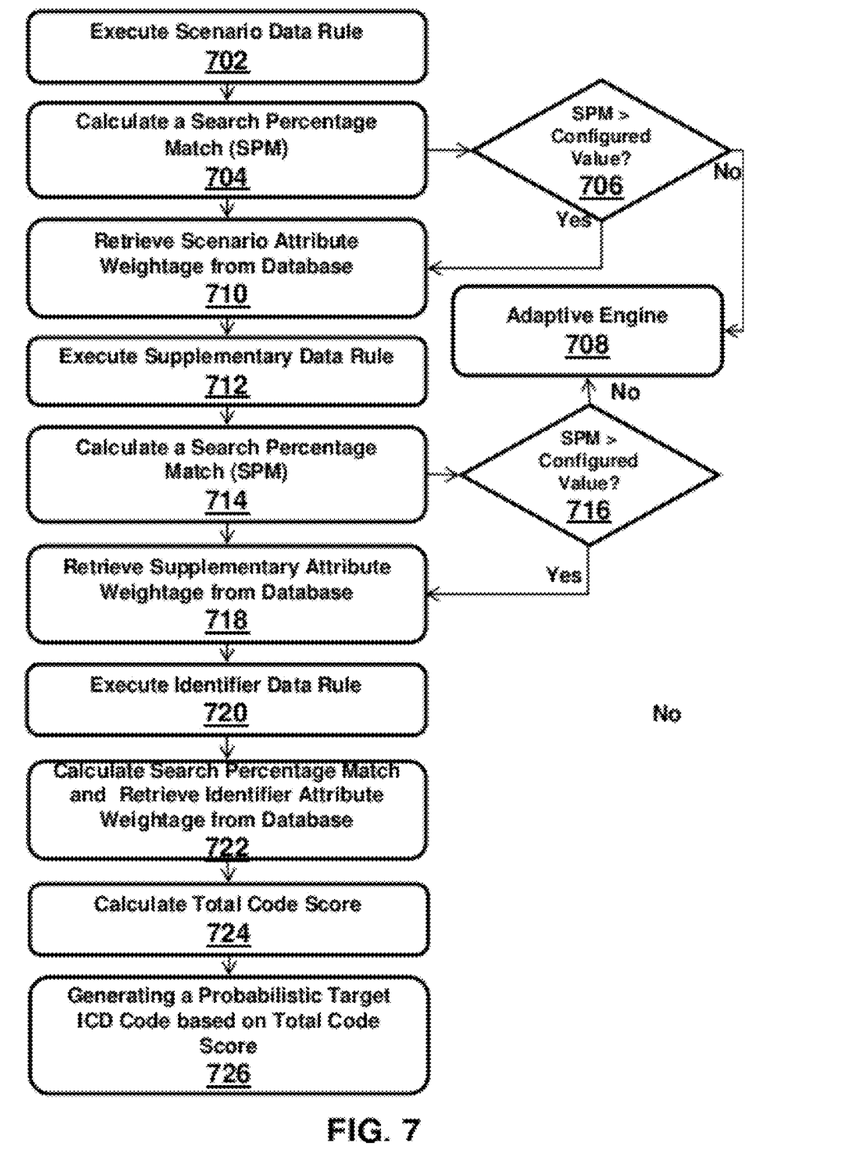
FIG. 7 is a schematic illustration depicting the automatic location a source ICD code to a target ICD code.

FIG. 7 is schematic illustration depicting the method used to automatically find one or more target ICD code. A source code is manually entered or a file serving as the input 302 is parsed to obtain the source ICD code 304. By parsing medical notes, the system obtains further additional parameters such as a body part or a treatment, for example. Tokens 306 are generated using the token module 204. Step 702 invokes the scenario data rule 504. The scenario which gets a maximum hit for the scenario tokens is selected by the system and a search percentage match is calculated 704 for the selected scenario. To avoid false positive results the system can be configured to search within the scenario slop. The scenario slop acts as a boundary within which the search should be carried out. The system can be configured to select one or more scenarios if the search percentage matches above the configured value 706. If the search percentage match is below a configured value then the system directs the user to an adaptive engine 708 to obtain relevant correlation parameters during manual override, which can then be used to update the rules. If the search percentage match is above the configured value then the scenario weightage is retrieved 710 for the selected scenarios. Every target ICD code is assigned a weightage, the value of which is stored in a database. The weightage is assigned based on the degree of the match of the description of that code with the medical notes i.e. the target ICD code whose description matches the medical notes to the greatest degree is assigned the highest weightage. As per sequence every choice rule in the selected scenarios is picked, step 712 invokes the supplementary data rule 506. Supplementary data rule is executed on all target codes in the applicable choice list to determine which target ICD codes constitute the subset for which this rule is applicable. For each target ICD code in this subset supplementary tokens are searched on the medical notes and a search percentage match is calculated 714. If the supplementary tokens are found within the medical notes and the search percentage is above a configured value 716 then step 718 retrieves the supplementary weightage value from the database. The weightage is assigned based on the degree of the match of the description of that code with the medical notes i.e. the target ICD code whose description matches the medical notes to the greatest degree is assigned the highest weightage. If supplementary tokens are found and the search percentage match is above the configured value, step 720 invokes the identifier data rule 508. The identifier tokens are unique values for each of the target ICD codes. For a code to be picked, the identifier tokens are to be found near the supplementary tokens. A search percentage match is calculated by comparing the identifier tokens to the medical notes and identifier weightage is retrieved from the database 722. If a choice list has just one choice, then update the supplementary and identifier weightages are updated as 100. There may be situations where the target ICD code has a single scenario. Virtual scenarios are applicable in such cases.

If a source ICD code has only one equivalent target ICD code, then the scenario weightage is updated with search percentage as 100. In such cases, for ease of searching, a very large choice list is divided into a number of logically similar groups. Each such group is called a virtual scenario. A virtual scenario search is carried out and supplementary data rule is executed. Supplementary weightage is updated based on the search percentage. If supplementary data rule is successfully executed, identifier data rule is invoked and search percentage value and identifier weightage is accordingly updated. The actual weightage or the total code score 724 added is a % of weightage of the attribute to the summation of weightages of all three attributes:

$$\text{Total Code Score for a Target ICD Code} = \Sigma_{i=1 \text{ to } N}(\text{SearchPercentageMatch} * \text{Weighatge}/\Sigma_{i=1 \text{ to } N} \text{Weightage}_i)$$

Where:
Weightage 1β=Scenario Weightage
Weightage 2=Supplementary Weightage
Weightage 3=Choice list Weightage
In case of Virtual Scenarios:
Weightage 1=Scenario Weightage/2
Weightage 2=Supplementary Weightage
Weightage 3=Choice list Weightage The target ICD code is then generated 726 based on the total code score. If there are more than one target ICD codes, then the choices are filtered by thresholds (not shown in figure). There are two kinds of threshold; upper threshold and lower threshold. The threshold details are retrieved from a database. The total code score of each target ICD code is compared with the threshold values. For a particular choice list, the target ICD code above the upper threshold is selected if it is the above the upper threshold and if all the other codes are below the lower threshold. Alternatively, the system can also be configured to pick all codes which are between the lower threshold and the upper threshold.

In one embodiment of the disclosure, the conversion rules may be configured by a payer, for example, to process claims based on a set of conditions. Additional information such as age, geography, hospital name etc can be obtained from the claims or medical notes and this information can be compared with the type of diagnosis or procedures handled by the hospital, for example, to find a potential target ICD code.

Having described and illustrated the principles of the disclosure with reference to described embodiments and accompanying drawings, it will be recognized by a person skilled in the art that the described embodiments may be modified in arrangement without departing from the principles described herein.

What is claimed is:

1. A computer-implemented method for a probabilistic target mapping of a source International Classification of Diseases (ICD) code to one or more target ICD codes, the method comprising:
   generating scenario tokens, supplementary tokens and identifier tokens from the target ICD codes descriptions, wherein multiple equivalent target ICD codes descriptions correspond to a source ICD code;
   calculating an attribute score for each of:
   a. at least one of a scenario, wherein the at least one of a scenario is determined by comparing the scenario tokens with a set of configured parameters;
   b. at least one of a choice list determined using supplementary tokens; and
   c. at least one of the choice list determined using identifier tokens;
   calculating a total code score for each of the target ICD codes descriptions; and
   generating a probabilistic target ICD code based on the total code score.

2. The method of claim 1, wherein the scenario tokens, supplementary tokens and the identifier tokens are compared to one or more configured parameters.

3. The method of claim 1, wherein at least one scenario is determined by comparing the scenario tokens to medical notes.

4. The method of claim 1, wherein at least one choice list is determined by comparing the supplementary tokens and the identifier tokens to medical notes.

5. The method of claim 1, wherein the attribute score is calculated using a search percentage match and an attribute weightage.

6. The method of claim 5, wherein the search percentage match is calculated based on a search performed within a scenario slop, a supplementary slop and an identifier slop.

7. The method of claim 5, wherein the attribute weightages for each of the scenario and the choice list is retrieved from a database.

8. The method of claim 1, wherein the total score is calculated for at least one of the scenario data, the supplementary data and the identifier data or a combination of the scenario data, the supplementary data and the identifier data.

9. The method of claim 1, wherein the scenario tokens are generated from target ICD code descriptions.

10. The method of claim 1, wherein the scenario tokens, the supplementary tokens and the identifier tokens are generated using a synonyms database.

11. The method of claim 1, wherein the supplementary tokens are generated by searching for a common sub-sequence from at least one of the choice list.

12. The method of claim 1, wherein the identifier tokens are generated by selecting at least one singular word within the proximity of the common sub-sequence used to generate the supplementary tokens.

13. The method of claim 1, wherein the probabilistic target ICD code is identified by comparing the total code score for each of the target ICD codes with a lower threshold value and an upper threshold value, wherein the lower threshold value and the upper threshold values are retrieved from a database.

14. The method of claim 1, wherein a virtual scenario is created in the event the target code descriptions contains non-multiple scenarios.

15. The method of claim 1, further comprising an adaptive engine to adapt particulars entered by a user, wherein the adaptive engine is triggered in the event the system is unable to determine at least one of the scenario data.

16. The method of claim 15, wherein the particulars entered by a user is adapted in subsequent mapping of the source ICD code to the one or more target ICD code.

17. The method of claim 1, wherein the source ICD code is one of an ICD-9 code and an ICD-10 code.

18. The method of claim 1, wherein each of the one or more target ICD codes is one of an ICD-9 code and an ICD-10 code.

19. An automated system for a probabilistic target mapping of a source International Classification of Diseases (ICD) code to one or more target ICD codes, the system comprising:
   a token generating module for generating scenario tokens, supplementary tokens and identifier tokens from the target ICD codes descriptions, wherein multiple equivalent target ICD codes descriptions correspond to a source ICD code;
   a processor configured to calculate an attribute score for each of:
   a. at least one of a scenario, wherein the at least one of a scenario is determined by comparing the scenario tokens with a set of configured parameters;
   b. at least one of a choice list determined using supplementary tokens; and
   c. at least one of the choice list determined using identifier tokens;
   calculate a total code score for each of the equivalent target ICD codes; and
   a code generator module for generating a probabilistic target ICD code based on the total code score.

20. The automated system of claim 19, further comprising a rule engine to compare the scenario tokens, supplementary tokens and the identifier tokens to one or more configured parameters.

21. The automated system of claim 20, wherein the rule engine compares the scenario tokens, supplementary tokens and the identifier tokens to medical notes.

22. The automated system of claim 19, wherein the attribute score is calculated using a search percentage match and an attribute weightage.

23. The automated system of claim 22, wherein the search percentage match is calculated based on a search performed within a scenario slop, a supplementary slop and an identifier slop.

24. The automated system of claim 22, wherein the attribute weightages for each of the scenario and the choice list is retrieved from a database.

25. The automated system of claim 19, wherein the total score is calculated for at least one of the scenario data, the supplementary data and the identifier data or a combination of the scenario data, the supplementary data and the identifier data.

26. The automated system of claim 19, wherein the scenario tokens are generated from target ICD code descriptions.

27. The automated system of claim 19, wherein the supplementary tokens are generated by searching for a common sub-sequence from at least one of the choice list.

28. The automated system of claim 19, wherein the identifier tokens are generated by selecting at least one singular word within the proximity of the common sub-sequence used to generate the supplementary tokens.

29. The automated system of claim 19, wherein the scenario tokens, the supplementary tokens and the identifier tokens are generated using a synonyms database.

30. The automated system of claim 19, wherein the probabilistic target ICD code is identified by comparing the total code score for each of the target ICD codes with a lower threshold value and an upper threshold value, wherein the lower threshold value and the upper threshold value is retrieved from the database.

31. The automated system of claim 19, further comprising an adaptive engine to adapt particulars entered by a user, wherein the adaptive engine is triggered in the event the system is unable to determine at least of the scenario data.

32. The automated system of claim 31, wherein the particulars entered by a user is adapted in subsequent mapping of the source ICD code to the one or more target ICD code.

33. The automated system of claim 19, wherein a virtual scenario is created in the event the target code descriptions contains a large number of target codes.

34. The automated system of claim 19, wherein the source ICD code is one of an ICD-9 code and an ICD-10 code.

35. The automated system of claim 19, wherein each of the one or more target ICD codes is one of an ICD-9 code and an ICD-10 code.

* * * * *